United States Patent
Sengun

(10) Patent No.: US 10,603,024 B2
(45) Date of Patent: Mar. 31, 2020

(54) DEVICES, SYSTEMS, AND METHODS FOR MOVING TISSUE WITHIN A BODY

(71) Applicant: Medos International Sarl, Le Locle (CH)

(72) Inventor: Mehmet Z. Sengun, Canton, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 236 days.

(21) Appl. No.: 15/185,193

(22) Filed: Jun. 17, 2016

(65) Prior Publication Data

US 2017/0360471 A1    Dec. 21, 2017

(51) Int. Cl.
*A61B 17/02* (2006.01)
*A61B 17/00* (2006.01)
*A61B 90/00* (2016.01)

(52) U.S. Cl.
CPC .... *A61B 17/0218* (2013.01); *A61B 17/00234* (2013.01); *A61B 2017/00349* (2013.01); *A61B 2090/036* (2016.02)

(58) Field of Classification Search
CPC .......... A61B 2017/00349; A61B 17/06; A61B 17/06104; A61B 17/2841; A61B 17/34; A61B 2017/06009; A61B 2017/06019; A61B 17/0469; A61B 17/0483; A61B 17/0485; A61B 17/2909; A61F 2/962; A61F 2/966
See application file for complete search history.

(56) References Cited

U.S. PATENT DOCUMENTS

| | | | |
|---|---|---|---|
| 4,774,948 A * | 10/1988 | Markham | A61B 90/39 606/185 |
| 5,158,565 A * | 10/1992 | Marcadis | A61B 17/34 600/567 |
| 5,895,395 A | 4/1999 | Yeung | |
| 5,910,148 A * | 6/1999 | Reimels | A61B 17/0483 606/139 |
| 7,896,879 B2 | 3/2011 | Solsberg et al. | |
| 7,942,898 B2 | 5/2011 | Ewers et al. | |
| 9,066,770 B2 | 6/2015 | Justis | |
| 2004/0127915 A1 | 7/2004 | Fleenor et al. | |
| 2006/0264994 A1 | 11/2006 | Schomer et al. | |
| 2007/0198019 A1 | 8/2007 | Schomer et al. | |
| 2011/0190793 A1 | 8/2011 | Nobles et al. | |
| 2012/0109185 A1* | 5/2012 | Fleenor | A61B 17/2909 606/205 |
| 2014/0236194 A1 | 8/2014 | Deutsch et al. | |

(Continued)

*Primary Examiner* — Sarah W Aleman

(57) ABSTRACT

In general, devices, systems, and methods for relocating tissue during surgeries are provided. In one embodiment, a surgical apparatus is provided that includes a needle, a hook movably disposed in the needle, an actuator, and a slidable member. The needle can be percutaneously advanced through skin of a patient. The actuator can move the hook between two orientations, one being disposed entirely within the needle and another extending from the needle. The slidable member can slide along the needle and abut an exterior surface of the skin of the patient through which the needle is advanced. In use, the hook can engage tissue within the body of the patient when the hook extends from the needle. The surgical apparatus can then move the engaged tissue within the body of the patient, and the engaged tissue can be locked in position relative to the skin.

24 Claims, 4 Drawing Sheets

(56) References Cited

U.S. PATENT DOCUMENTS

2014/0276779 A1 9/2014 Grunewald
2015/0320417 A1 11/2015 Stewart et al.
2016/0051261 A1 2/2016 Centeno et al.

* cited by examiner

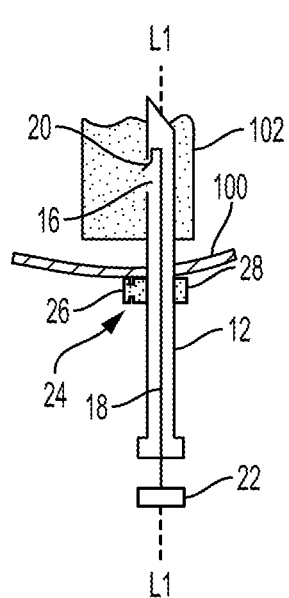
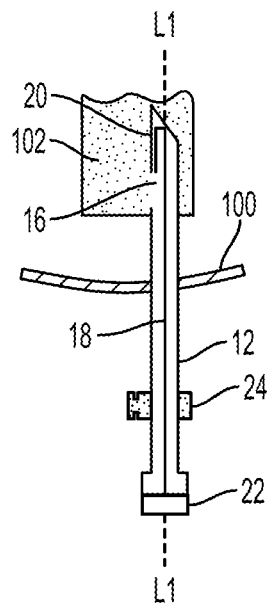
FIG. 13    FIG. 14
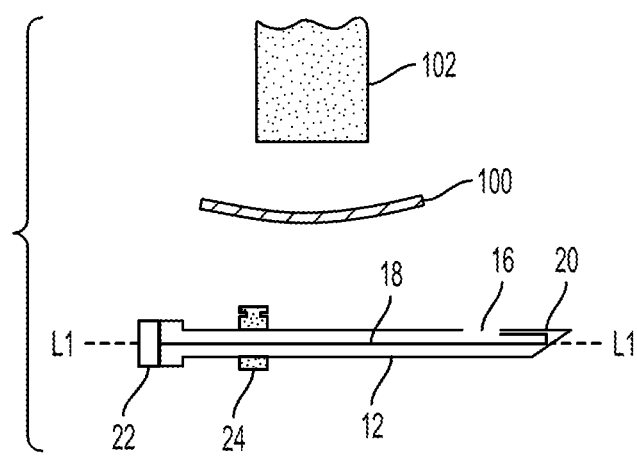
FIG. 15

DEVICES, SYSTEMS, AND METHODS FOR MOVING TISSUE WITHIN A BODY

FIELD

The present disclosure relates generally to devices, systems, and methods for moving tissue within a body.

BACKGROUND

Surgeons may desire to reposition or relocate tissue during a variety of different surgeries for varied reasons, for example to allow access to a surgical site or to remove an obstruction. For another example, during an arthroscopic surgery, a surgeon may want to relocate soft tissue, maintain the new position during the surgery, and/or keep the soft tissue under tension.

Movement of tissue can currently be achieved through use of graspers or a retractor. However, these approaches require an incision be made in a patient to allow access to the graspers or retractor and introduction of a cannula to allow insertion of the graspers or retractor, which complicates the surgery and requires either the surgeon or an assistant to constantly hold the graspers or retractor.

Movement of tissue can also be currently accomplished through use of sutures. However, this approach can prolong and complicate the surgery, for example by having to repeat movement of tissue multiple times and because the use of sutures is time-consuming.

Accordingly, there remains a need for improved devices, systems, and methods for moving tissue within a body.

SUMMARY

In general, devices, systems, and methods for moving tissue within a body are provided.

In one aspect, a surgical apparatus is provided that in one embodiment includes a needle, a hook, an actuator, and a slidable member. The needle has an inner cavity, a longitudinal axis, and an opening formed through a sidewall thereof in a distal portion of the needle. The needle is configured to be percutaneously advanced through skin of a patient. The hook is movably disposed in the inner cavity. The actuator is configured to be selectively actuated to move the hook between a first orientation and a second orientation. The hook in the first orientation is entirely disposed within the inner cavity at a first position along the longitudinal axis of the needle, and the hook in the second orientation extends from the inner cavity through the opening so as to be at least partially located outside of the needle and at a second position along the longitudinal axis of the needle. The second position is proximal to the first position. The slidable member is mounted on the needle. The slidable member is configured to be slid along the needle to abut an exterior surface of the skin through which the needle is percutaneously advanced.

The surgical apparatus can vary in any number of ways. For example, the actuator can be configured to slide proximally along the needle to move the hook from the first orientation to the second orientation and to slide distally along the needle to move the hook from the second orientation to the first orientation. For another example, the actuator can include a hub at a proximal-most end of the needle that is configured to be pulled proximally to move the hook from the first orientation to the second orientation and to be pushed distally to move the hook from the second orientation to the first orientation. For yet another example, the actuator when actuated can be configured to move a predetermined distance between a first position and a second position, where the actuator in the first position corresponds to the hook in the first orientation and the actuator in the second position corresponds to the hook in the second orientation. For still another example, the opening can be formed through the sidewall at a location proximal to a distal most end of the needle. In still another example, the hook in the first orientation can be substantially parallel to the longitudinal axis of the needle, and the hook in the second orientation can be at an angle transverse to the longitudinal axis of the needle.

In another aspect, a surgical method is provided that in one embodiment includes percutaneously advancing an elongate shaft of a surgical device into a body of a patient. The surgical device has a selectively deployable hook disposed within an inner cavity thereof. The method also includes actuating an actuator of the surgical device to move the hook in a proximal direction, thereby causing the hook to extend through an opening in a sidewall of the elongate shaft. The method also includes manipulating the surgical device to cause the hook extending through the opening to engage tissue within the body of the patient, and manipulating the surgical device to move the engaged tissue within the body of the patient.

The method can have any number of variations. For example, actuating the actuator can include moving the actuator in a proximal direction. For another example, actuating the actuator can include moving the actuator a predetermined distance relative to the elongate shaft to extend the hook a predetermined amount out of the opening. For another example, the actuator can include one of a knob slidable within a slot formed in the elongate shaft, and a hub that is proximal to the elongate shaft. In yet another example, the elongate shaft can have a longitudinal axis, and the hook can extend through the opening at an angle transverse to the longitudinal axis. For still another example, the method can include, after manipulating the surgical device to move the engaged tissue, locking the surgical device in position to hold the tissue in a substantially fixed position. In yet another example, the method can include, after manipulating the surgical device to move the engaged tissue, actuating the actuator again to move the hook in a distal direction, thereby causing the hook to no longer extend through the opening.

In another embodiment, a surgical method is provided that includes percutaneously passing a needle through skin into a body of a patient. The method also includes, after the percutaneous passage, causing a hook disposed within the needle to move through an opening formed through a sidewall of the needle to be located at least partially outside of the needle. The method includes causing the hook located at least partially outside of the needle to engage tissue within the body of the patient. The method also includes moving the hook having the tissue engaged therewith, thereby causing the engaged tissue to move within the body of the patient.

The method can have any number of variations. For example, causing the hook disposed within the needle to move can include actuating an actuator that is in a proximal portion of the needle located outside the body of the patient. For another example, after moving the engaged tissue, the method can include causing the hook to move through the opening and again be disposed within the needle. In another example, the method can include locking the moved and engaged tissue in position relative to the skin. In at least some embodiments, the locking can include moving a slidable lock into contact with an exterior surface of the skin.

BRIEF DESCRIPTION OF DRAWINGS

This invention will be more fully understood from the following detailed description taken in conjunction with the accompanying drawings, in which:

FIG. 13 is a cross-sectional side view of the tool of FIG. 12 with the slidable member positioned against the skin;

FIG. 14 is a cross-sectional side view of the tool of FIG. 13 with the hook no longer hooked in the tissue and the slidable member retracted away from the skin; and FIG. 15 is a cross-sectional side view of the tool of FIG. 14 removed from the skin and the tissue.

DETAILED DESCRIPTION

Figure 1:
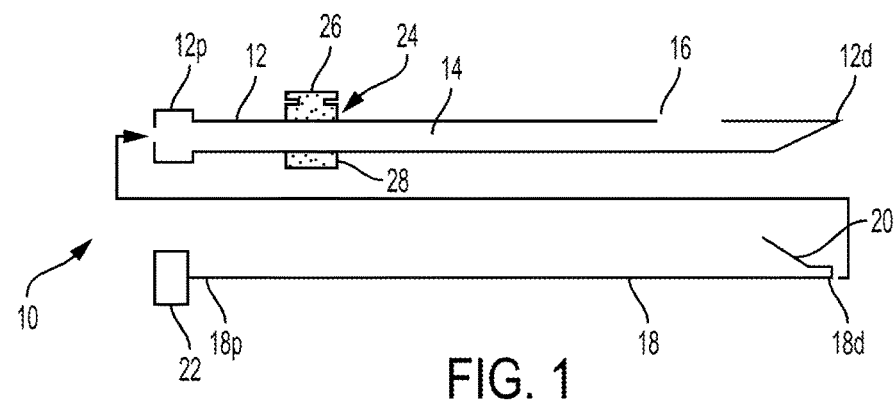
FIG. 1 is a cross-sectional side view of one embodiment of a tissue manipulation tool including a needle, a hook, and a slidable member, the tool being in a disassembled state.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary devices, systems, and methods for moving tissue within a body are provided. In general, a surgical apparatus can be configured to move tissue. The apparatus can include a needle and a hook. The needle can have an inner cavity, in which the hook can be movably disposed. The needle can also have an opening formed through a sidewall in a distal portion of the needle. The apparatus can include an actuator configured to move the hook between a first position and a second position. The hook can be entirely disposed within the needle in the first position, and the hook can extend through the opening of the needle in the second position. The hook in the second position can be configured to engage tissue. The apparatus can be configured to move (e.g., by hand, via another tool, using a robotic surgical system, etc.) to move the engaged tissue. The tissue can thus be retracted. The apparatus can include a locking mechanism to facilitate holding the tissue in its moved location.

The surgical apparatus may efficiently relocate and reposition tissue within the patient with minimal harm done to the patient due to the percutaneous nature of the needle. The hook can be disengaged from the tissue and the needle can be retracted from the patient with only minor damage done to any surrounding skin and tissue. Traditionally, moving tissue requires invasive graspers and/or other tools that risk and/or cause substantial damage to the tissue being moved and to surrounding tissue. The surgical apparatuses described herein may move tissue multiple times with little to no harm done to the patient due to minor damage caused both by removing and reinserting the needle multiple times and deploying and retracting the hook multiple times. A user may thus ensure ideal placement of tissue without needing to weigh the consequences of imperfect tissue placement with the potential dangers of increased harm done to a patient. The surgical apparatuses described herein may allow tissue movement to be completed rapidly, only causing a minor delay in any operation to engage and move tissue. The speed with which tissue may be relocated may lead to shorter surgical times and more efficient surgeries. Being able to lock the needle in position may allow greater freedom and convenience during a surgery. Under traditional methods of tissue movement, a surgeon or an assistant must continuously manipulate tools and/or must continuously maintain and monitor the position of relocated tissue. The apparatuses described herein may allow, once tissue is in a desired location and the needle is locked in position, the surgeon or assistant to focus his or her attention on other aspects of the surgery, and the hands of the surgeon or assistant can be free to perform other tasks without worrying about the position or location of any relocated tissue. Use of the surgical apparatuses may thus save time, increase efficiency, and/or reduce harm to the patient caused by movement of tissue.

Figure 2:
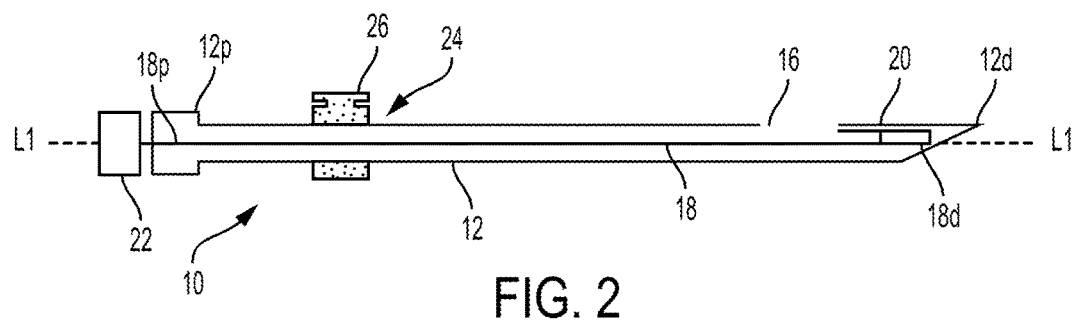
FIG. 2 is a cross-sectional side view of the tool of FIG. 1 in an insertion configuration.
Figure 3:
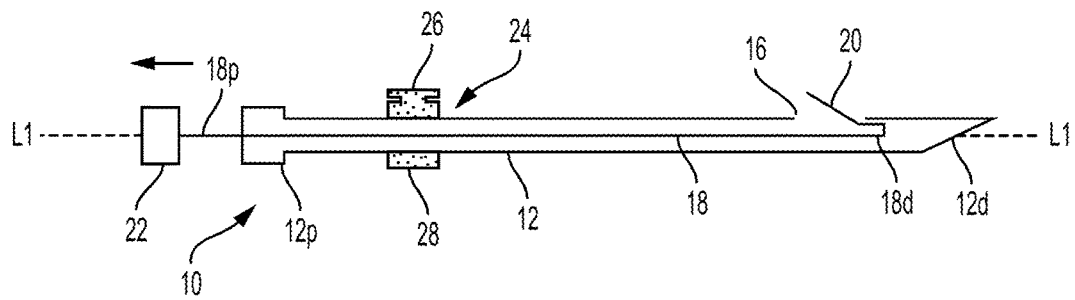
FIG. 3 is a cross-sectional side view of the tool of FIG. 1 in a deployed configuration.

FIGS. 1-3 illustrate one embodiment of a surgical apparatus 10 for moving tissue. The surgical apparatus 10 has a needle 12 that is configured to be percutaneously advanced through skin of a patient. The apparatus 10 also has a wire 18 that is configured to be at least partially disposed in the needle 12 and is configured to slidably move within the needle 12 to selectively deploy a hook 20 of the wire 18 through an opening 16 of the needle 12. A slidable member 24 is mounted on the needle 12 and is configured to slide along a length of the needle 12 and lock the needle 18, and consequently the hook 20, in a selected position relative to the needle 12.

The needle 12 has an inner cavity 14, a proximal end 12p, a distal end 12d, and an opening 16 formed through as sidewall thereof between the proximal end 12p and the distal end 12d. The distal end 12d of the needle 12 is pointed and sharp to facilitate percutaneous entry of the surgical apparatus 10 into a patient's body without a need to create an incision in the patient's body to allow percutaneous advancement of the surgical apparatus 10 into the patient. Instead of requiring the incision, the distal end 12d can create a puncture itself through the patient's skin.

The opening 16 can have a variety of shapes, such as a circle, an oval, a rectangle, a slit, etc. A diameter of the opening 16 is greater than a diameter of the hook 20 such that the hook 20 can pass therethrough. In an exemplary embodiment, the shape and size of the opening 16 allow the hook 20 to pass therethrough. The opening 16 is in a distal portion of the needle 12 near the distal end 12d thereof. On the opening 16 being in the distal portion of the needle 12 may help to ensure that the opening 16 (and thus the hook 20) is in a patient's body when the surgical apparatus 10 is disposed within the patient's body when the hook 20 is deployed and/or so that an amount of advancement of the surgical apparatus 10 into the patient's body may be minimized.

The needle 12 has a length in a range of about 4 to 5 inches, but a variety of lengths can be used. The needle 12 is an 18 gauge needle, but various diameters can be used for the needle 12. In an exemplary embodiment, the diameter of the needle 12 is such that the hole it creates through skin does not require stitching to close, for example a diameter of up to about 2 mm, and is such that it will allow movement of the wire 18 within the needle 12 while allowing the wire 18 to be large enough to successfully move tissue. In at least some embodiments, the needle 12 can both be used as a spinal needle and to move tissue. For example, the needle 12 can be used in rotator cuff surgery to, for instance, move a cuff to position the cuff at a point where a surgeon wants to attach the cuff.

The wire 18 has the hook 20 at a distal end 18d of the wire 18. The hook 20 is an integral part of the wire 18 and is formed from the wire 18 being folded back upon itself. In other embodiments, the hook 20 can be a separate element from the wire 18 and be fixed thereto in any of a variety of ways, such as by welding, adhesive, etc.

An actuator 22 is disposed on a proximal end 18p of the wire 18. While the actuator 22 is a pull hub in this illustrated embodiment, a variety of actuators can be used, such as a thumb-activated trigger, a hook, a loop, etc. The wire 18 is movable between a first orientation, illustrated in FIG. 2, and a second orientation, illustrated in FIG. 3, relative to the needle 12. As illustrated in FIG. 2, the hook 20 in the first orientation is disposed entirely within the inner cavity 14 of the needle 12. As illustrated in FIG. 3, the hook 20 in the second orientation is located partially outside the inner cavity 14 of the needle 12 by extending through the opening 16 formed in the needle 12. In other embodiments, the hook 20 can be entirely located outside of the needle's inner cavity 14 in the second orientation. In general, in the second orientation, at least a free end of the hook 20 is located outside of the inner cavity 14, and hence outside of the needle 12 entirely, to allow the hook 20 to engage tissue. As also illustrated in FIG. 3, the actuator 22 is movable with respect to the needle 12 to move the hook 20 between the first and second orientations. The actuator 22 is configured to move proximally to move the hook 20 from the first orientation to the second orientation and is configured to move distally to move the hook 20 from the second orientation to the first orientation.

The hook 20 is biased to an open configuration, which is illustrated in FIGS. 1 and 3, where the hook 20 flares away from the wire 18 such that a narrowest point is on the distal end 18d and a widest point is toward the proximal end 18p of the wire 18. When the hook 20 is moved via the actuator 22 toward the second orientation, the hook 20 will automatically extend through the opening 16 due to the biasing to the open configuration. Because the hook 20 is narrowest at the distal end 18d and widest toward the proximal end 18p of the wire 18, an angle of the hook 20 will ease re-entry of the hook 20 back into the needle 12 through the opening 16 when the hook 20 is moved from outside of the needle 12 to be back within the needle 12, e.g., when the hook 20 is moved from the second orientation to the first orientation. An inner wall of the needle 12 that defines the inner cavity 14 contains the hook 20 therein in a compressed configuration when the wire 18 is in the first orientation. The inner wall of the needle 12 counteracts the bias of the hook 20 and holds the hook 20 in the compressed position to facilitate percutaneous entry of the apparatus 10 into a patient's body without the hook 20 protruding through the opening 16 and potentially snagging on or otherwise damaging tissue and/or other matter. With the hook 20 in both the first orientation and the second orientation, the wire 18 and the needle 12 extend along a shared longitudinal axis L1. In the first orientation, the hook 20 also extends substantially parallel to the longitudinal axis L1. A person skilled in the art will appreciate that the hook 20 may not extend precisely parallel to the longitudinal axis L1 but nevertheless be considered substantially parallel to the longitudinal axis L1 due to any one or more factors, such as manufacturing tolerances and sensitivity of measurement devices. In the second orientation, the hook 20 is oriented transversely relative to the longitudinal axis L1.

The wire 18 has a diameter in a range of about 0.010 to 0.015 inches, but the diameter can vary in other embodiments. In an exemplary embodiment, the diameter of the wire 18 allows the wire 18 to be freely movable within the needle 12 and to be thick enough that the hook 20 can hook into tissue instead of slicing or "cheese-wiring" therethrough. The wire 18 can be made from any one or more of a variety of materials, such as spring steel or superelastic material. In an exemplary embodiment, the material forming the wire 18 is not overly malleable to prevent the wire 18 from bending too much when the hook 20 moves tissue, and the material is not too brittle to prevent the wire 18 from breaking when the hook 20 moves tissue.

The slidable member 24 is movable along the exterior surface of the needle 12, e.g., along the longitudinal axis L1, and the slidable member 24 can be locked at any selected point along the exterior surface of the needle 12. The slidable member 24 is configured to abut an exterior surface of skin through which the apparatus 10 is percutaneously advanced. The slidable member 24 can take any of a variety of forms, for example a hub 26 and body 28 combination that is kept locked against the needle 12 by a spring (obscured within the slidable member 24 in FIGS. 1-3) disposed within the body 28, and can be slidable along the needle 12 by pressing the hub 26 against the body 28 to compress the spring. Releasing the hub 26 can release the compression of the spring and automatically lock the slidable member 24 at the point along the needle 12 at which the slidable member 24 is located when the hub 26 is released. For another example, the slidable member 24 can include a nut threadably engaged with a thread formed on the exterior surface of the needle 12. The nut can be rotated in one direction to move proximally along the needle 12 and can be rotated in the opposite direction to move distally along the needle 12. The nut's rotation can be stopped anywhere along the thread of the needle so as to lock at any selected point along the needle 12. For another example, the slidable member 24 can include a pin configured to be selectively engaged with one of a plurality of depressions longitudinally aligned and formed in the exterior surface of the needle 12. The pin can be selectively inserted into any one of the depressions to lock the slidable member in position thereat. The pin can be removed from and inserted into a depression in any of a variety of ways, such as by being coupled to a spring that biases the pin toward the needle 12, with the pin being pullable away from the needle 12 to allow movement of the pin between depressions.

Figure 4:
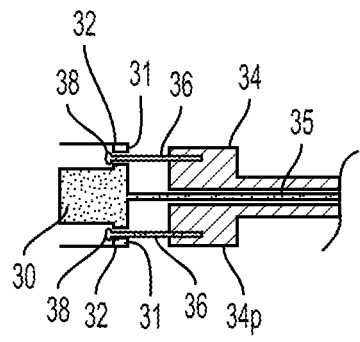
FIG. 4 is a cross-sectional side view of a proximal portion of another embodiment of a tissue manipulation tool in a deployed configuration.
Figure 5:
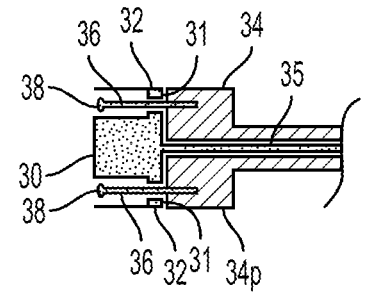
FIG. 5 is a cross-sectional side view of the tool of FIG. 4 in an insertion configuration.

FIGS. 4 and 5 illustrate another embodiment of an actuator 30 that can be used in place of the actuator 22 or as an actuator in another embodiment of a surgical apparatus including a needle and wire as described herein. The actuator 30 is coupled to a proximal end of a wire 35 and a proximal end 34p of a needle 34. In general, the wire 35 and the needle 34 can be configured and used similar to that discussed above regarding the wire 18 and the needle 12 of the surgical apparatus 10 of FIGS. 1-3. First and second pins 36 extend proximally from the proximal end 34p of the needle 34, and the pins 36 each have a head 38 positioned on a proximal end thereof. The pins 36 are movably positioned in channels 31 of the actuator 30, and the heads 38 abut inner surfaces 32 of the actuator 30 when the actuator 30 is in a proximal-most position corresponding to when the wire 35 is in its second orientation. FIG. 5 shows the actuator 30 in a distal-most position, abutting the proximal end 34p of the needle 34, corresponding to when the wire 35 is in its first orientation. The actuator 30 is proximally movable with respect to the needle 34, and FIG. 4 shows the actuator 30 moved to the proximal-most position in a direction away from the needle 34. The pins 36 align the actuator 30 as the actuator moves, and the heads 38 abut the inner surface 32 of the actuator 30 and stop the actuator 30 in the proximal-most position, preventing the actuator 30 from moving too far away from the needle 34. The hook (not shown) near the distal end of the wire 35 may thus be moved to a predictable position through an opening (not shown) formed in a sidewall of the needle 34. In other words, the hook can be predictably moved from its first orientation to the second orientation by the pins 36 stopping movement of the actuator 30 after moving a predetermined distance, which is defined by a length of the pins 36. The actuator 30 is configured to not be rotatable relative to the needle 34 to maintain proper alignment between the actuator 30 and the needle 34 as the actuator 30 is moved proximally and distally. The actuator 30 can be configured to not rotate in any of a variety of ways, such as by the pin 36 holding the actuator 30 in a substantially fixed rotational position relative to the needle 34. Although two pins 36 are used in this illustrated embodiment, another number of pins can be used, e.g., one, three, four, etc.

Figure 6:
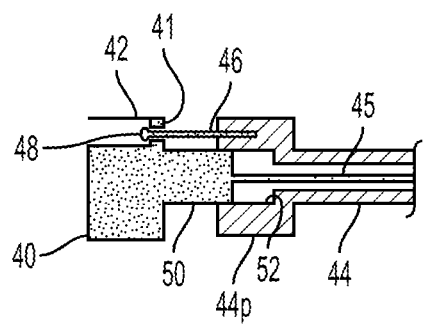
FIG. 6 is a cross-sectional side view of a proximal portion of yet another embodiment of a tissue manipulation tool in a deployed configuration.
Figure 7:
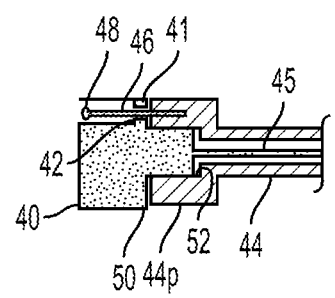
FIG. 7 is cross-sectional side view of the tool of FIG. 6 in an insertion configuration.

FIGS. 6 and 7 illustrate another embodiment of an actuator 40 that can be used in place of the actuator 22 or as an actuator in another embodiment of a surgical apparatus including a needle and wire as described herein. The actuator 40 is coupled to a proximal end of a wire 45 and a proximal end 44p of a needle 44. In general, the wire 45 and the needle 44 can be configured and used similar to that discussed above regarding the wire 18 and the needle 12 of the surgical apparatus 10 of FIGS. 1-3. A single pin 46 extends proximally from the proximal end 44p of the needle 44, and the pin 46 has a head 48 positioned on a proximal end thereof. The pin 46 extends through a channel 41 of the actuator 40, and the head 48 abuts an inner surface 42 of the actuator 40 when the actuator 40 is in a proximal-most position corresponding to when the wire 45 is in its second orientation. A distal portion 50 of the actuator 40 is movably disposed in a cavity 52 formed in the proximal end 44p of the needle 44. FIG. 7 shows the actuator 40 in a distal-most position, corresponding to when the wire 45 is in its first orientation, abutting the proximal end 44p of the needle 44. The actuator 40 is proximally movable with respect to the needle 44, and FIG. 6 shows the actuator 40 moved to the proximal-most position away from the needle 44. The head 48 abuts the inner surface 42 of the actuator 40 and stops the actuator 40 in the proximal-most position after moving a predetermined distance, thereby preventing the actuator 40 from moving too far away from the needle 44. The actuator 40 is configured to not be rotatable relative to the needle 44 to maintain proper alignment between the actuator 40 and the needle 44 as the actuator 40 is moved proximally and distally. The actuator 40 can be configured to not rotate in any of a variety of ways, such as by the pin 46 holding the actuator 40 in a substantially fixed rotational position relative to the needle 44. The distal portion 50 of the actuator 40 has a non-circular cross-sectional shape, which may further help prevent rotation thereof relative to the needle 44. Although a single pin 46 is used in this illustrated embodiment, another number of pins can be used, e.g., two, three, four, etc.

Figure 8:
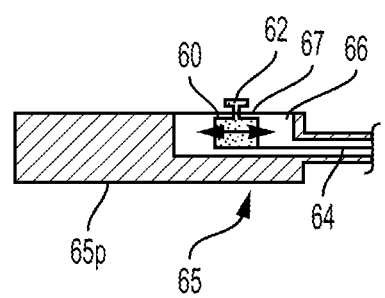
FIG. 8 is a cross-sectional side view of a proximal portion of yet another embodiment of a tissue manipulation tool.

FIG. 8 illustrates another embodiment of an actuator 60 that can be used in place of the actuator 22 or as an actuator in another embodiment of a surgical apparatus including a needle and wire as described herein. The actuator 60 is disposed within a chamber 66 formed in a proximal end 65p of a needle 65, and the actuator 60 is coupled to a wire 64. In general, the needle 65 and the wire 64 can be configured and used similar to that discussed above regarding the wire 18 and the needle 12 of the surgical apparatus 10 of FIGS. 1-3. A thumb tab 62 of the actuator 60 extends through a slot 67 formed in the proximal end 65p of the needle 65 that is in communication with the chamber 66. The actuator 60 is slidable within the slot 67 with respect to the needle 65. The actuator 60 is movable between a distal-most position, corresponding to when the wire 64 is in its first orientation, and a proximal-most position, corresponding to when the wire 64 is in its second orientation, within the chamber 66 in response to movement of the thumb tab 62.

One embodiment of a method of moving tissue using a surgical apparatus is illustrated in FIGS. 9-15. Although the method of FIGS. 9-15 is illustrated with respect to the surgical apparatus 10 of FIGS. 1-3, any of the surgical apparatuses described herein can be similarly used.

Figure 9:
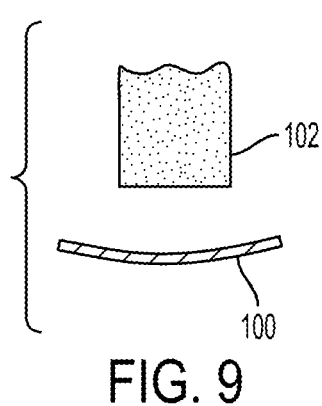
FIG. 9 is a cross-sectional side view of skin and tissue of a patient.
Figure 10:
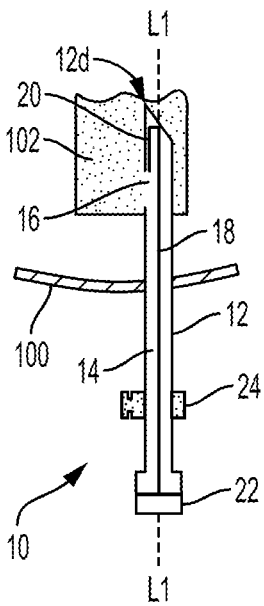
FIG. 10 is a cross-sectional side view of the tool of FIG. 2 advanced through the skin and into the tissue of FIG. 9.
Figure 11:
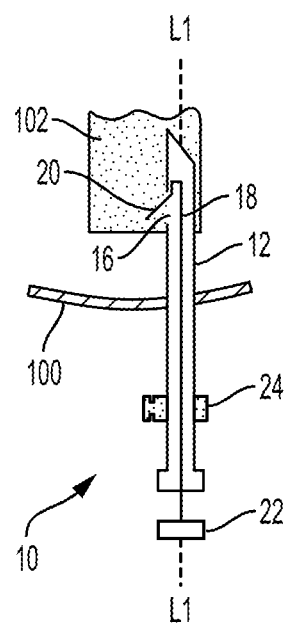
FIG. 11 is a cross-sectional side view of the tool of FIG. 10 hooked into the tissue.

FIG. 9 illustrates skin 100 and tissue 102 of a patient. As shown in FIG. 10, the distal end 12d of the needle 12 of the surgical apparatus 10 pierces the skin 100, and the apparatus 10 is advanced in a distal direction, thereby percutaneously passing a distal portion of the apparatus 10 through the skin 100 and into the tissue 102 of the patient that underlies the skin 100. The hook 20 of the wire 18 is in the first orientation entirely disposed within the inner cavity 14 of the needle 12. The actuator 22 is then retracted proximally, as illustrated in FIG. 11, causing the hook 20 of the wire 18 to move to the second orientation so as to extend through the opening 16 and be located at least partially outside of the needle 12 and at a position proximal to the hook's position when in the first orientation.

Figure 12:
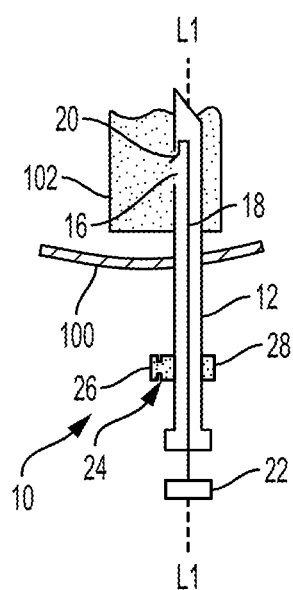
FIG. 12 is a cross-sectional side view of the tool of FIG. 11 with the tissue moved.

As the hook 20 moves outside of the needle 12 in response to the actuation of the actuator, the hook 20 engages the tissue 12, as shown in FIG. 12. The apparatus 10 can then be moved by a surgeon, causing the tissue 102 engaged by the hook 20 to move within the body of the patient, as shown in FIG. 13. When the hooked tissue 102 has been moved to a desired location, the slidable member 24 mounted on the needle 12 can be slid distally along the length of the needle 12 by pressing the hub 26 to compress the spring and moving the slidable member 24 distally. The slidable member 24 can be slid distally to abut an exterior surface of the skin 100 and locked against the needle 12, e.g., by releasing the hub 26, thereby locking the needle 18, and consequently the hook 20, in a selected position relative to the tissue 102 and ensuring the tissue 102 remains in a substantially fixed position at the desired location without continued interaction from the surgeon or an assistant, e.g., without the apparatus 10 needing to be handheld in position. The tissue 102 being at the desired location can be verified prior to and/or after locking the slidable member 24, such as through visualization of the tissue 102 using a scope. A person skilled in the art will appreciate that the tissue 102 may not remain at precisely the same position but nevertheless be considered fixed at the position due to any one or more factors, such as flexibility of the skin 100. The location of the needle 12 and the tissue 102 can be maintained until the tissue 102 needs to again be adjusted in position, either by being moved again while hooked by the hook 20 or by being released from the hook 20 and allowed to return to its original location. The tissue 102 and/or the needle 12 can be moved, engaged, reengaged, and/or released multiple times during an operation with minimal or no harm done to the patient. During an operation, multiple needles 12 can be used by the surgeon to hook and move the tissue 102 and/or other tissue(s) depending on the surgical procedure in question and the preferences of the surgeon.

To release the hook 20 from the tissue 102, the slidable member 24 is released from its position abutting the exterior surface of the skin 100 by being slid proximally along the needle 12. The actuator 22 is then advanced distally relative to the needle 12, causing the hook 20 to move back to the first orientation in which it is entirely disposed within the inner cavity 14 of the needle 12. The tissue 102 is released from the hook 20 as the hook 20 returns to the first orientation, as illustrated in FIG. 14. The apparatus 10 can then be retracted proximally from the tissue 102 and out of the skin 100 of the patient, as illustrated in FIG. 15. The apparatus 10 can then optionally be percutaneously introduced into the patient again to move the tissue 102 again and/or to move other tissue(s) of the patient.

A person skilled in the art will appreciate that the implementations described herein have application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical apparatus, comprising:
   a needle having an inner cavity, a longitudinal axis, and an opening formed through a sidewall thereof in a distal portion of the needle, the needle being configured to be percutaneously advanced through skin of a patient;
   a hook movably disposed in the inner cavity;
   an actuator configured to be actuated a first predetermined distance in a proximal direction to move the hook from a first orientation and a second orientation and configured to be actuated a second predetermined distance in a distal direction to move the hook from the second orientation to the first orientation, the actuator being in a proximal-most position corresponding to the hook being in the second orientation, the actuator being in a distal-most position corresponding to the hook being in the first orientation, the hook in the first orientation being entirely disposed within the inner cavity at a first position along the longitudinal axis of the needle, and the hook in the second orientation extending from the inner cavity through the opening so as to be at least partially located outside of the needle and at a second position along the longitudinal axis of the needle, the second position being proximal to the first position, the actuator being prevented from moving beyond the second predetermined distance distally through stopping contact with a proximal end of the needle;
   a pin extending proximally from the proximal end of the needle the pin having a proximal head, the pin being movably positioned in a channel formed in the actuator, the proximal head being enclosed proximally and radially by the actuator, and the proximal head being configured to abut an inner surface of the actuator when the hook is in the second orientation to prevent the actuator from moving beyond the first predetermined distance proximally; and
   a slidable member mounted on the needle, the slidable member being configured to be slid along the needle to abut an exterior surface of the skin through which the needle is percutaneously advanced.

2. The apparatus of claim 1, wherein the opening is formed through the sidewall at a location proximal to a distal-most end of the needle.

3. The apparatus of claim 1, wherein the hook in the first orientation is distal to the opening.

4. The apparatus of claim 1, wherein the hook in the first orientation is substantially parallel to the longitudinal axis of the needle, and the hook in the second orientation is at an angle transverse to the longitudinal axis of the needle.

5. The apparatus of claim 1, wherein the pin is radially offset from the longitudinal axis of the needle and is configured to prevent the actuator from rotating relative to the needle.

6. The apparatus of claim 1, wherein the hook is biased to an open configuration angled away from the longitudinal axis of the needle, and the hook is configured to automatically move to the open configuration extending through the opening when the hook is moved to the second orientation.

7. The apparatus of claim 6, wherein the actuator is configured to be selectively slid to return the hook from the second orientation to the first orientation, and the hook is configured to automatically move from the open configuration to a compressed configuration in which the hook is compressed within the inner cavity in the first orientation.

8. The apparatus of claim 1, wherein the hook has a narrowest point on a distal end thereof and a widest point toward a proximal end of the hook.

9. The apparatus of claim 1, wherein the needle has a proximal cavity formed in the proximal end thereof, and a distal portion of the actuator is configured to be seated in the proximal cavity of the needle at least when the hook is in the first orientation such that rotation of the actuator relative to the needle is prevented.

10. The apparatus of claim 9, wherein the proximal cavity is in communication with the inner cavity of the needle, a diameter of the proximal cavity at a distal end thereof is greater than a diameter of the inner cavity at a proximal end thereof, and a diameter of the distal portion at a distal end thereof is greater than the diameter of the inner cavity at the proximal end thereof.

11. The apparatus of claim 9, wherein the distal portion of the actuator and the proximal cavity of the needle are aligned with the longitudinal axis of the needle, and the first pin is radially offset from the longitudinal axis of the needle.

12. The apparatus of claim 1, wherein the pin includes first and second pins.

13. The apparatus of claim 1, wherein the pin is a single pin.

14. A surgical method, comprising:
percutaneously advancing an elongate shaft of a surgical device into a body of a patient, the surgical device having a selectively deployable hook disposed within an inner cavity thereof;
moving an actuator of the surgical device to move the hook a predetermined distance in a proximal direction until a head on a proximal end of a pin abuts an inner surface of the actuator, the pin extending proximally from a proximal end of the needle and being movably positioned in a channel formed in the actuator, the head being enclosed proximally and radially by the actuator, thereby causing the hook to extend through an opening in a sidewall of the elongate shaft;
manipulating the surgical device to cause the hook extending through the opening to engage tissue within the body of the patient; and
manipulating the surgical device to move the engaged tissue within the body of the patient.

15. The method of claim 14, wherein moving the actuator the predetermined distance in the proximal direction extends the hook a predetermined amount out of the opening.

16. The method of claim 14, wherein the elongate shaft has a longitudinal axis, and the hook extends through the opening at an angle transverse to the longitudinal axis.

17. The method of claim 14, further comprising, after manipulating the surgical device to move the engaged tissue, locking the surgical device in position to hold the tissue in a substantially fixed position.

18. The method of claim 14, further comprising, after manipulating the surgical device to move the engaged tissue, moving the actuator again to move the hook in a distal direction, thereby causing the hook to no longer extend through the opening.

19. The method of claim 14, wherein the actuator is non-rotatable relative to the elongate shaft.

20. The method of claim 14, wherein percutaneously advancing the elongate shaft of the surgical device into the body of the patient comprises piercing skin of the body with a distal end of the elongate shaft of the surgical device to form a hole through the skin, and then piercing tissue underlying the skin.

21. A surgical method, comprising:
percutaneously passing a needle through skin into a body of a patient;
after the percutaneous passage, sliding an actuator proximally away from the needle to cause a hook disposed within the needle to move through an inner lumen of the needle until the hook moves through an opening formed through a sidewall of the needle to be located at least partially outside of the needle, a head on a proximal end of a pin contacting an inner surface of the actuator in response to maximum proximal movement of the actuator being reached, the pin extending proximally from a proximal end of the needle and being movably positioned in a channel firmed in the actuator, the head being enclosed proximally and radially by the actuator;
causing the hook located at least partially outside of the needle to engage tissue within the body of the patient; and
moving the hook having the tissue engaged therewith, thereby causing the engaged tissue to move within the body of the patient.

22. The method of claim 21, further comprising locking the moved and engaged tissue in position relative to the skin.

23. The method of claim 22, wherein the locking includes moving a slidable lock into contact with an exterior surface of the skin.

24. The method of claim 21, further comprising, after moving the engaged tissue, causing the hook to move through the opening and again be disposed within the needle.

* * * * *